United States Patent
Doris et al.

(10) Patent No.: US 11,092,567 B2
(45) Date of Patent: Aug. 17, 2021

(54) BIOSENSOR ELECTRODE HAVING THREE-DIMENSIONAL STRUCTURED SENSING SURFACES

(71) Applicant: International Business Machines Corporation, Armonk, NY (US)

(72) Inventors: Bruce B. Doris, Slingerlands, NY (US); Eugene J. O'Sullivan, Nyack, NY (US); Sufi Zafar, Briarcliff Manor, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 414 days.

(21) Appl. No.: 15/464,418

(22) Filed: Mar. 21, 2017

(65) Prior Publication Data

US 2018/0275093 A1 Sep. 27, 2018

(51) Int. Cl.
*G01N 27/414* (2006.01)
*C12Q 1/6837* (2018.01)

(52) U.S. Cl.
CPC ..... *G01N 27/4145* (2013.01); *G01N 27/4146* (2013.01); *G01N 27/4148* (2013.01); *C12Q 1/6837* (2013.01)

(58) Field of Classification Search
CPC .......... G01N 27/4145; G01N 27/4146; G01N 27/4148; C12Q 1/6837
See application file for complete search history.

(56) References Cited

U.S. PATENT DOCUMENTS

| 5,057,447 A * | 10/1991 | Paterson | ........... H01L 29/40114 438/253 |
| 7,659,149 B2 | 2/2010 | Yoo et al. | |
| 7,948,015 B2 | 5/2011 | Rothberg et al. | |
| 8,373,206 B2 | 2/2013 | Potter | |

(Continued)

FOREIGN PATENT DOCUMENTS

| DE | 102008009826 A1 | 8/2009 |
| GB | 218344 A | 6/1987 |

(Continued)

OTHER PUBLICATIONS

Doris et al., "Biosensor Electrode Having Three-Dimensional Structured Sensing Surfaces," U.S. Appl. No. 15/803,908, filed Nov. 6, 2017.

(Continued)

*Primary Examiner* — Robert J Eom
(74) *Attorney, Agent, or Firm* — Cantor Colburn LLP; Erik Johnson

(57) ABSTRACT

Embodiments of the invention are directed to a sensor that includes a sensing circuit and a probe communicatively coupled to the sensing circuit. The probe includes a three-dimensional (3D) sensing surface coated with a recognition element and configured to, based at least in part on the 3D sensing surface interacting with a predetermined material, generate a first measurement. In some embodiments, the 3D sensing surface is shaped as a pyramid, a cone, or a cylinder to increase the sensing surface area over a two-dimensional (2D) sensing surface. In some embodiments, the 3D sensing surface facilitates penetration of the 3D sensing surface through the wall of the biological cell.

10 Claims, 14 Drawing Sheets

(56) References Cited

U.S. PATENT DOCUMENTS

| | | |
|---|---|---|
| 8,409,867 B2 | 4/2013 | Bansal et al. |
| 10,556,398 B2 | 2/2020 | Haynes et al. |
| 2004/0136866 A1 | 7/2004 | Pontis et al. |
| 2006/0054941 A1 | 3/2006 | Lu et al. |
| 2006/0197118 A1 | 9/2006 | Migliorato et al. |
| 2008/0319298 A1 | 12/2008 | Huys et al. |
| 2009/0061451 A1 | 3/2009 | Achim et al. |
| 2011/0233512 A1 | 9/2011 | Yang et al. |
| 2013/0019688 A1 | 1/2013 | Tung et al. |
| 2013/0158378 A1 | 6/2013 | Berger et al. |
| 2014/0353172 A1 | 12/2014 | Melosh et al. |
| 2015/0137794 A1 | 5/2015 | Lieber et al. |
| 2016/0374585 A1 | 12/2016 | Fonash et al. |

FOREIGN PATENT DOCUMENTS

| | | |
|---|---|---|
| JP | S6283641 A | 4/1987 |
| JP | 2004085392 A | 3/2004 |
| JP | 2011133234 A | 7/2011 |
| JP | 2013516613 A | 5/2013 |
| JP | 2014530366 A | 11/2014 |
| WO | 2014210306 A1 | 12/2014 |
| WO | 2016009228 A | 1/2016 |

OTHER PUBLICATIONS

List of IBM Patents or Patent Applications Treated as Related; Date Filed: Mar. 21, 2017, 2 pages.

Zafar et al., "Optimization of pH Sensing Using Silicon Nanowire Field Effect Transistors with HfO2 as the Sensing Surface," Nanotechnology 22 (2011) 405501, IOP Publishing, 7 pgs.

International Search Report and Written Opinion dated Jun. 27, 2018 in PCT/IB2018/051870 (10 pages).

Doris et al., "Biosensor Electrode Having Three-Dimensional Structured Sensing Surfaces," U.S. Appl. No. 16/539,332, filed Aug. 13, 2019.

List of IBM Patents or Patent Applications Treated as Related; Date Filed: Aug. 13, 2019, 2 pages.

\* cited by examiner

BIOSENSOR ELECTRODE HAVING THREE-DIMENSIONAL STRUCTURED SENSING SURFACES

BACKGROUND

The present invention relates in general to biosensors. More specifically, the present invention relates to fabrication methods, resulting structures, and methods of use for a biosensor probe/electrode having a three-dimensional (3D) structured sensing surface.

Biosensors are used to measure various types of physical and chemical parameters. In a known biosensor configuration, a field effect transistor (FET) acts as a transducer separated by an insulator layer (e.g. $SiO_2$) from a biological recognition element (a.k.a., a biosensor electrode). The recognition element can be a biofilm material such as a receptor, enzyme, antibody, DNA or other type of capturing molecule that is biologically specific for the target analyte. The recognition element can be configured to detect, for example, ion concentration (e.g., pH) or the concentration of target biomolecules (e.g., DNA, microRNA, enzymes, antibodies, and the like). The phrase "target analyte" and variations thereof will be used herein to refer to an ion, a target molecule, or any other biological substance.

Once the targeted ions and/or molecules bind to the recognition element, the charge distribution at the surface of the recognition element changes, which causes a corresponding change in the electrostatic surface potential at a gate of the FET. This change in the surface potential applies a voltage to the FET's gate, which results in a voltage drop (Vgs) across the gate and the source. When the applied gate voltage causes Vgs to reach the threshold voltage (Vth), current starts to flow from the source to the drain. The Vth is defined as the value of Vgs at which a sufficient density of mobile electrons or holes gather in the channel to allow the channel to conduct. The value of Vgs and the resulting source to drain current flow are proportional to the targeted ions and/or molecules that bind to the recognition element.

The change in current (or conductance) through the FET can be measured and analyzed to detect the analyte that is binding to the biological recognition element. A processor-based biosensor reader device receives the FET drain current, provides further processing as needed, and displays the results in user-friendly forms that are more easily measured and quantified. Other types of transducers can be used to convert the detection of the analyte to other types of measureable outputs such as optical signals, physiochemical signals, piezoelectric signals, electrochemical signals, and the like.

Biosensor performance can be evaluated according to several factors. For example, biosensor performance can be evaluated based on the lowest concentration of the target analyte that is required before the biosensor can produce an output that is clearly distinguishable from noise in the measurement. Biosensor performance can also be evaluated based on the sensitivity range of the recognition element, which can be expressed as low end sensitivity and high end sensitivity. Using pH concentration as an example, a given biosensor can have a low end sensitivity and a high end sensitivity of 2-12 pH. The low end sensitivity is similar to the previously described lowest concentration of the target analyte that is required before the biosensor can produce an output that is clearly distinguishable from noise in the measurement. The high end sensitivity is reached when the recognition element becomes saturated so that no binding sites remain for absorption of the analyte. Thus, a biosensor cannot detect actual values that are lower than the low end biosensor sensitivity or higher than the high end biosensor sensitivity. Biosensor performance can also be evaluated based on the required sample size. Small sensors such as FET-based biosensors generally minimize the required sample size and are often preferred in medical applications where the sample typically is a volume of a patient's bodily fluid such as blood.

The above-described biosensor performance factors can be improved by improving how efficiently analytes bind to the recognition element, which is influenced at least in part by characteristics of the recognition element's sensing surface. In FET biosensors, the recognition element can also function as the FET gate. The combined FET gate and recognition element structure has a flat, two-dimensional (2D) and substantially planar sensing surface.

SUMMARY

Embodiments of the invention are directed to a sensor that includes a sensing circuit and a probe communicatively coupled to the sensing circuit. The probe includes a three-dimensional (3D) sensing surface coated with a recognition element and configured to, based at least in part on the 3D sensing surface interacting with a predetermined material, generate a first measurement. The above-described embodiments of the invention provide more sensing surface area, which improves the efficiency with which analytes of interest bind to the sensing surface, improves the signal strength, and improves the signal to noise ratio.

Embodiments of the invention s are directed to a method of forming a sensor. The method includes forming a sensing circuit and a probe structure that includes a 3D sensing surface structure coated with a recognition element. The probe is communicatively coupled to the sensing circuit, and the 3D sensing surface structure is configured to, based at least in part on the 3D sensing surface structure interacting with a predetermined material, generate a first measurement. The above-described embodiments of the invention provide more sensing surface area, which improves the efficiency with which analytes of interest bind to the sensing surface, improves the signal strength, and improves the signal to noise ratio.

Embodiments of the invention are directed to a method of using a sensor. The method includes accessing a sample and exposing the sample to a sensor, where the sensor includes a sensing circuit communicatively coupled to a probe structure having a 3D sensing surface structure coated with a recognition element. Based at least in part on the 3D sensing surface structure contacting a predetermined material in the sample, the 3D sensing surface structure generates a first measurement. Based at least in part on the first measurement, the sensing circuit generates a sensing circuit output that is proportional to a predetermined characteristic of the predetermined material. The above-described embodiments of the invention provide more sensing surface area, which improves the efficiency with which analytes of interest bind to the sensing surface, improves the signal strength, and improves the signal to noise ratio.

Additional features and advantages are realized through the techniques described herein. Other embodiments and aspects are described in detail herein. For a better understanding, refer to the description and to the drawings.

BRIEF DESCRIPTION OF THE DRAWINGS

The subject matter which is regarded as the present invention is particularly pointed out and distinctly claimed in the claims at the conclusion of the specification. The foregoing and other features and advantages are apparent from the following detailed description taken in conjunction with the accompanying drawings in which:

Figure 1A:
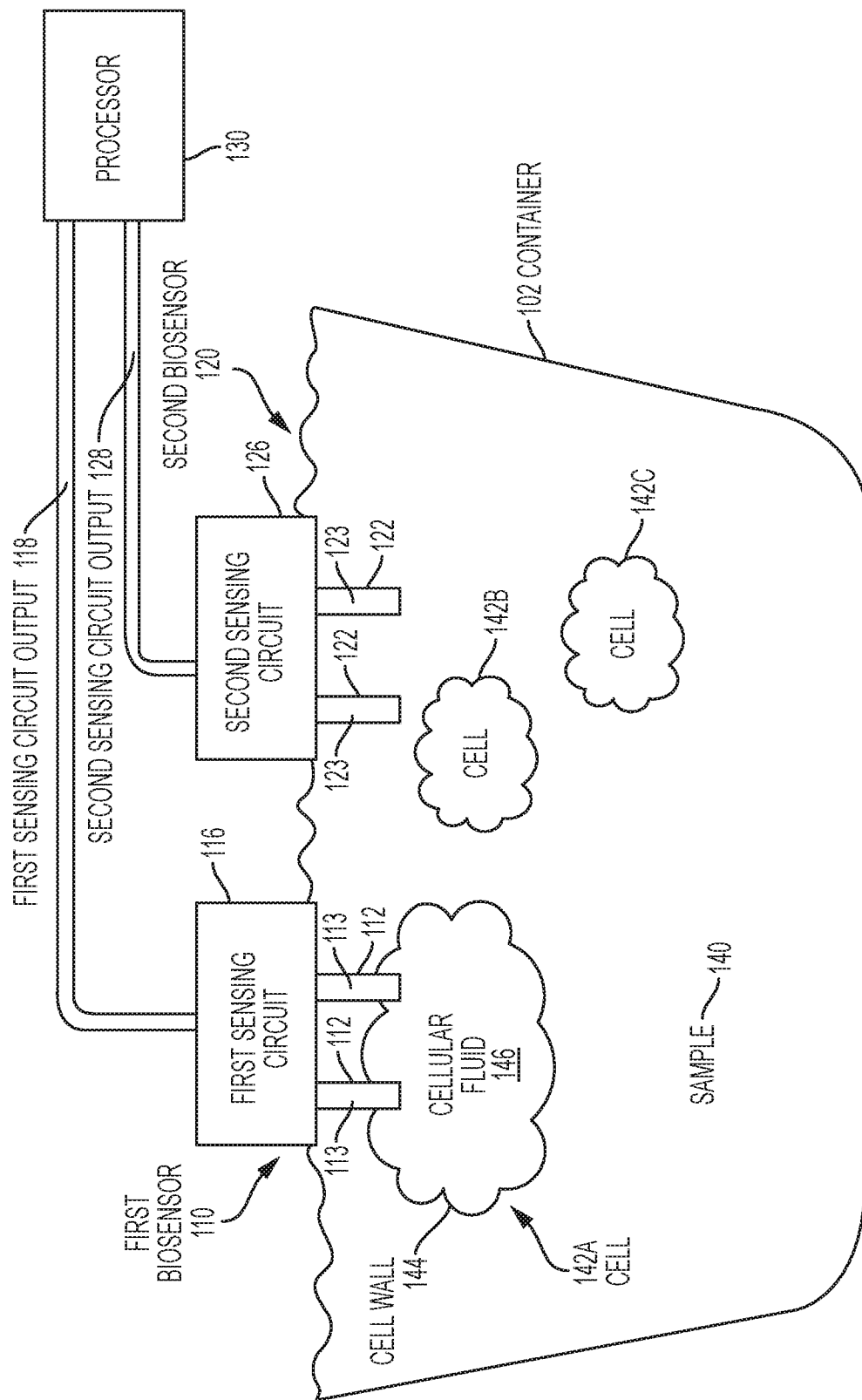
FIG. 1A depicts a schematic diagram of a biosensor system having 3D nanoprobe electrodes according to one or more embodiments of the invention.

In the accompanying figures and following detailed description of the disclosed embodiments, the various elements illustrated in the figures are provided with three or four digit reference numbers. The leftmost digit(s) of each reference number corresponds to the figure in which its element is first illustrated.

DETAILED DESCRIPTION

Various embodiments of the present invention are described herein with reference to the related drawings. Alternative embodiments can be devised without departing from the scope of this invention. It is noted that various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper," "lower," "right," "left," "vertical," "horizontal," "top," "bottom," and derivatives thereof shall relate to the described structures and methods, as oriented in the drawing figures. The terms "overlying," "atop," "on top," "positioned on" or "positioned atop" mean that a first element, such as a first structure, is present on a second element, such as a second structure, where intervening elements such as an interface structure can be present between the first element and the second element. The phrase "direct contact" means that a first element, such as a first structure, and a second element, such as a second structure, are connected without any intermediary conducting, insulating or semiconductor layers at the interface of the two elements. The phrase "selective to," such as, for example, "a first element selective to a second element," means that a first element can be etched and the second element can act as an etch stop. The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to semiconductor device and integrated circuit (IC) fabrication may or may not be described in detail herein. Moreover, the various tasks and process steps described herein can be incorporated into a more comprehensive procedure or process having additional steps or functionality not described in detail herein. In particular, various steps in the manufacture of semiconductor devices and semiconductor-based ICs are well known and so, in the interest of brevity, many conventional steps will only be mentioned briefly herein or will be omitted entirely without providing the well-known process details.

By way of background, however, a more general description of the semiconductor device fabrication processes that can be utilized in implementing one or more embodiments of the present invention will now be provided. Although specific fabrication operations used in implementing one or more embodiments of the present invention can be individually known, the described combination of operations and/or resulting structures of the present invention are unique. Thus, the unique combinations of the operations described according to the present invention utilize a variety of individually known physical and chemical processes performed on a semiconductor (e.g., silicon) substrate, some of which are described in the immediately following paragraphs.

In general, the various processes used to form a microchip that will be packaged into an IC fall into four general categories, namely, film deposition (or film formation), removal/etching, semiconductor doping and patterning/lithography. Deposition is any process that grows, coats, or otherwise transfers a material onto the wafer. Available technologies include physical vapor deposition (PVD), chemical vapor deposition (CVD), plasma-enhanced chemical vapor deposition (PECVD), electrochemical deposition (ECD), molecular beam epitaxy (MBE), and more recently, atomic layer deposition (ALD) and plasma-enhanced atomic layer deposition (PEALD), among others.

Removal/etching is any process that removes material from the wafer. Examples include etch processes (either wet or dry), and chemical-mechanical planarization (CMP), and the like. A wet etch process, such as a buffered hydrofluoric acid (BHF) etch, is a material removal process that uses liquid chemicals or etchants to remove materials from a surface. A dry etch process, such as reactive ion etching (RIE), uses chemically reactive plasma to remove a material, such as a masked pattern of semiconductor material, by exposing the material to a bombardment of ions that dislodge portions of the material from the exposed surface. The plasma is generated under low pressure (vacuum) by an electromagnetic field.

Semiconductor doping is the modification of electrical properties by doping, for example, transistor sources and drains, generally by diffusion and/or by ion implantation. These doping processes are followed by furnace annealing or by rapid thermal annealing (RTA). Annealing serves to activate the implanted dopants. Films of both conductors (e.g., poly-silicon, aluminum, copper, etc.) and insulators (e.g., various forms of silicon dioxide, silicon nitride, etc.) are used to connect and isolate transistors and their components. Selective doping of various regions of the semiconductor substrate allows the conductivity of the substrate to be changed with the application of voltage. By creating structures of these various components, millions of transistors can be built and wired together to form the complex circuitry of a modern microelectronic device.

Semiconductor lithography is the formation of three-dimensional relief images or patterns on the semiconductor substrate for subsequent transfer of the pattern to the substrate. In semiconductor lithography, the patterns are formed by a light sensitive polymer called a photo-resist. To build the complex structures that make up a transistor and the many wires that connect the millions of transistors of a circuit, lithography and etch pattern transfer steps are repeated multiple times. Each pattern being printed on the wafer is aligned to the previously formed patterns and slowly the conductors, insulators and selectively doped regions are built up to form the final device.

Turning now to a description of technologies that are more specifically relevant to the present invention, transistors are semiconductor devices commonly found in a wide variety of ICs. A transistor is essentially a switch. When a voltage is applied to a gate of the transistor that is greater than a threshold voltage, the switch is turned on, and current flows through the transistor. When the voltage at the gate is less than the threshold voltage, the switch is off, and current does not flow through the transistor.

Semiconductor devices are formed using active regions of a wafer. The active regions are defined by isolation regions used to separate and electrically isolate adjacent semiconductor devices. For example, in an IC having a plurality of metal oxide semiconductor field effect transistors (MOSFETs), each MOSFET has a source and a drain that are formed in an active region of a semiconductor layer by implanting n-type or p-type impurities in the layer of semiconductor material. Disposed between the source and the drain is a channel (or body) region. Disposed above the body region is a gate electrode. The gate electrode and the body are spaced apart by a gate dielectric layer. Complementary metal oxide semiconductor (CMOS) is a technology that uses complementary and symmetrical pairs of p-type and n-type MOSFETs to implement logic functions.

Biosensors utilize electrochemical processes to detect a chemical state (e.g., pH), a change in a chemical state (e.g., a change in pH) or the presence of a biological substance (e.g., enzymes, antibodies, DNA, microRNA, and the like) by using a transducing element (e.g., a FET) to convert a detection event identified by a recognition element into an electrical signal.

Turning now to an overview of aspects of the present invention, embodiments of the invention provide a FET-based biosensor where the gate of the FET is shaped in a 3D nanoprobe structure such as a cylinder, a pyramid, a cone, or the like. The 3D nanoprobe can be coated with a recognition element (e.g., TiN) for measuring pH. The 3D nanoprobe can be coated with another recognition element (e.g., Au) or measuring biomolecules using thiol chemistry. For example, for detecting DNA, the gold surface can be functionalized with single strand DNA complimentary to the target DNA. In some embodiments, the 3D nanoprobe is provide with a width dimension (e.g., about 100 nm) and other structure features that facilitates the 3D nanoprobe penetrating a cellular wall to contacts and provide measurements from the fluid within the cell. A typical cell size is about 5×5 um². Accordingly, embodiments of the invention provide more sensing surface area, which improves the efficiency with which analytes of interest bind to the sensing surface, improves the signal strength, and improves the signal to noise ratio. Embodiments of the invention are also directed to methods for fabricating the FET and 3D nanoprobe structure, as well as methods for using the FET and 3D nanoprobe structure.

Turning now to a more detailed description of aspects of the present invention, FIG. 1A is a schematic diagram of a biosensor system 100 according to one or more embodiments of the invention. Biosensor system 100 includes a first biosensor 110, a second biosensor 120 and a processor 130, configured and arranged as shown. The first biosensor 110 includes a first sensing circuit 116 communicatively coupled to an array of 3D nanoprobes 112. The second biosensor 120 includes a second sensing circuit 126 communicatively coupled to an array of 3D nanoprobes 122. In embodiments of the invention, the sensing circuits 116, 126 can be implemented as one or more FETs. For ease of illustration and description, the biosensor system 100 includes two (2) biosensors 110, 120, and each biosensor 110, 120 includes one (1) sensing circuit 116, 126 and two (2) 3D nanoprobes 112, 122, configured and arranged as shown. However, the biosensor system 100 can include more than two biosensors 110, 120, and each biosensor 110, 120 can include more than one sensing circuit 116, 126 and any number of arrays having any number of 3D nanoprobes 112, 122. A first sensing circuit output 118 is supplied from the first sensing circuit 116 to the processor 130. A second sensing circuit output 126 is supplied from the second sensing circuit 126 to the processor 130.

The container 102 holds a sample 140 that includes multiple biological cells 142A, 142B, 142C. For ease of illustration and description, only three (3) biological cells are depicted in FIG. 1A. However, any number of biological cells can be in the sample 140. In some embodiments of the invention, the 3D nanoprobes 112, 122 are administered in vitro, and in some embodiments of the invention, the 3D nanoprobes 112, 122 are administered in vivo. In some embodiments, the 3D nanoprobes 112, 122 are administered percutaneously. Accordingly, the container 102 can take a variety of forms. For in vitro applications, the container 102 can be implemented as any structure configured to hold a sample (e.g., sample 140) for analysis by the biosensor system 100. For in vivo and/or percutaneous applications, the container 102 is the living organism to which the biosensor system 100 is being applied. Accordingly, in the descriptions provided herein, a reference to the container 102 includes all of the potential forms of the container 102.

The first biosensor 110 provides an example of an aspect of the invention where the 3D nanoprobes 112 penetrate through a wall of a biological cell (e.g., cellular wall 144 of biological cell 142A) and contacts fluid (e.g., intracellular fluid 146) within the biological cell. Each 3D nanoprobe 112, based at least in part on contacting a predetermined material in the fluid within the biological cell, generates a first measurement and provides that measurement directly or indirectly to the sensing circuit 116.

The second biosensor 120 provides an example of an aspect of the invention where the 3D nanoprobes 112 interacts with the sample 140 but does not necessarily penetrate through a wall of a biological cell (e.g., cellular wall 144 of biological cell 142A) and contact fluid (e.g., intracellular fluid 146) within the biological cell. Each 3D nanoprobe 122, based at least in part on contacting a predetermined material in the sample 140, generates a second measurement and provides that measurement directly or indirectly to the second sensing circuit 126.

The biosensor system 100 is used to measure various types of physical and chemical parameters. The operation of the first biosensor 110 is substantially the same as the operation of the second biosensor 120. Accordingly, the following description of the operation of the first biosensor 110 applies equally to the second biosensor 120. The sensing circuit or FET 116 acts as a transducer, and the 3D nanoprobes 112 can be coated with a material that allows them to function as a biological recognition element (a.k.a., a biosensor electrode). As described in greater detail subsequently herein, and in accordance with embodiments of the invention, the 3D nanoprobes 112 provide a greater sensing surface area (e.g., sensing surface area 113, 113A shown in FIGS. 1A and 1B) than known biosensor electrodes that are limited to 2D sensing surfaces. The sensing surface area 113 of the 3D nanoprobes 112 can be coated with a biofilm material such as a receptor, enzyme, antibody, DNA or other type of capturing molecule that is biologically specific for a target analyte. The sensing surface area of the 3D nanoprobes 112 can be configured to detect, for example, ion concentration (e.g., pH) or the concentration of target biomolecules (e.g., DNA, microRNA, enzymes, antibodies, and the like). As previously noted herein, the phrase "target analyte" and variations thereof will be used herein to refer to an ion, a target molecule, or any other biological substance.

Once the targeted ions and/or molecules bind to the sensing surface areas 113 of the 3D nanoprobes 112, the charge distribution at the sensing surface area of the 3D nanoprobes 112 changes, which causes a corresponding change in the electrostatic surface potential at a gate (not shown) of the FET sensing circuit 116. This change in the surface potential applies a voltage to the gate of the FET sensing circuit 116, which results in a voltage drop (Vgs) across the gate and the source of the FET sensing circuit 116. When the applied gate voltage causes Vgs to reach the threshold voltage (Vth), current starts to flow from the source to the drain of the FET sensing circuit 116. The Vth is defined as the value of Vgs at which a sufficient density of mobile electrons or holes gather in the FET channel to allow the channel to conduct. The value of Vgs and the resulting source to drain current flow through the FET sensing circuit 116 are proportional to the targeted ions and/or molecules that bind to the sensing surface area of the 3D nanoprobes 112.

The change in current (or conductance) through the FET sensing circuit 116 is transmitted as an FET sensing circuit output 118 to the processor 130 and analyzed to detect the analyte that is binding to the sensing surface area of the 3D nanoprobes 112. The processor 130 can be implemented as a biosensor reader device (not shown) that receives the FET sensing circuit output 118, provides further processing as needed, and displays the results in user-friendly forms that are more easily measured and quantified.

Figure 1B:
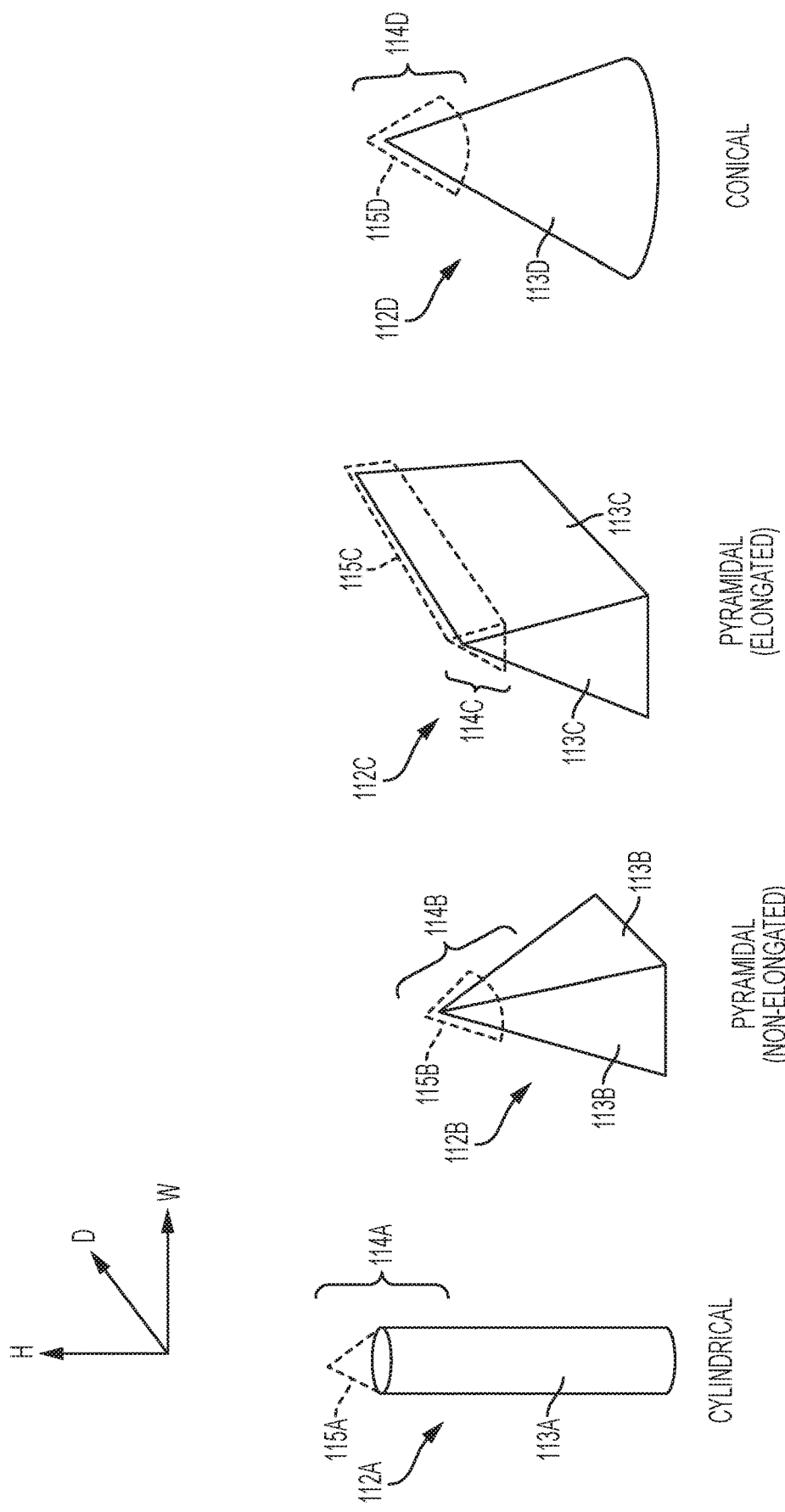
FIG. 1B depicts a block diagram showing example 3D nanoprobe biosensor electrode shapes according to one or more embodiments of the invention.

A more detailed description of the 3D nanoprobes 112, 122 shown in FIG. 1A will now be provided with reference to the example 3D nanoprobe shapes 112A, 112B, 112C, 112D shown in FIG. 1B. The 3D nanoprobe shapes 112A, 112B, 112C, 112D shown in FIG. 1B can be applied to either the first biosensor 110 or the second biosensor 120 shown in FIG. 1A. As shown in FIG. 1A, 3D nanoprobe 112A depicts an example of a cylindrical, 3D nanoprobe 112B depicts an example of a non-elongated pyramidal shape, 3D nanoprobe 112C depicts an example of a non-elongated pyramidal shape, and 3D nanoprobe 112 depicts an example of a conical shape. As shown, each 3D nanoprobe shapes 112A, 112B, 112C, 112D each include a height (H) dimension, a width (W) dimension and a depth (D) dimension. Each 3D nanoprobe shape 112A, 112B, 112C, 112D defines exterior surfaces 113A, 113B, 113C, 113D and apex regions 114A, 114B, 114C, 114D. In some embodiments, the apex regions 114A, 114B, 114C, 114D are configured to terminate at peaks 115A, 115B, 115C, 115D.

Figure 1C:
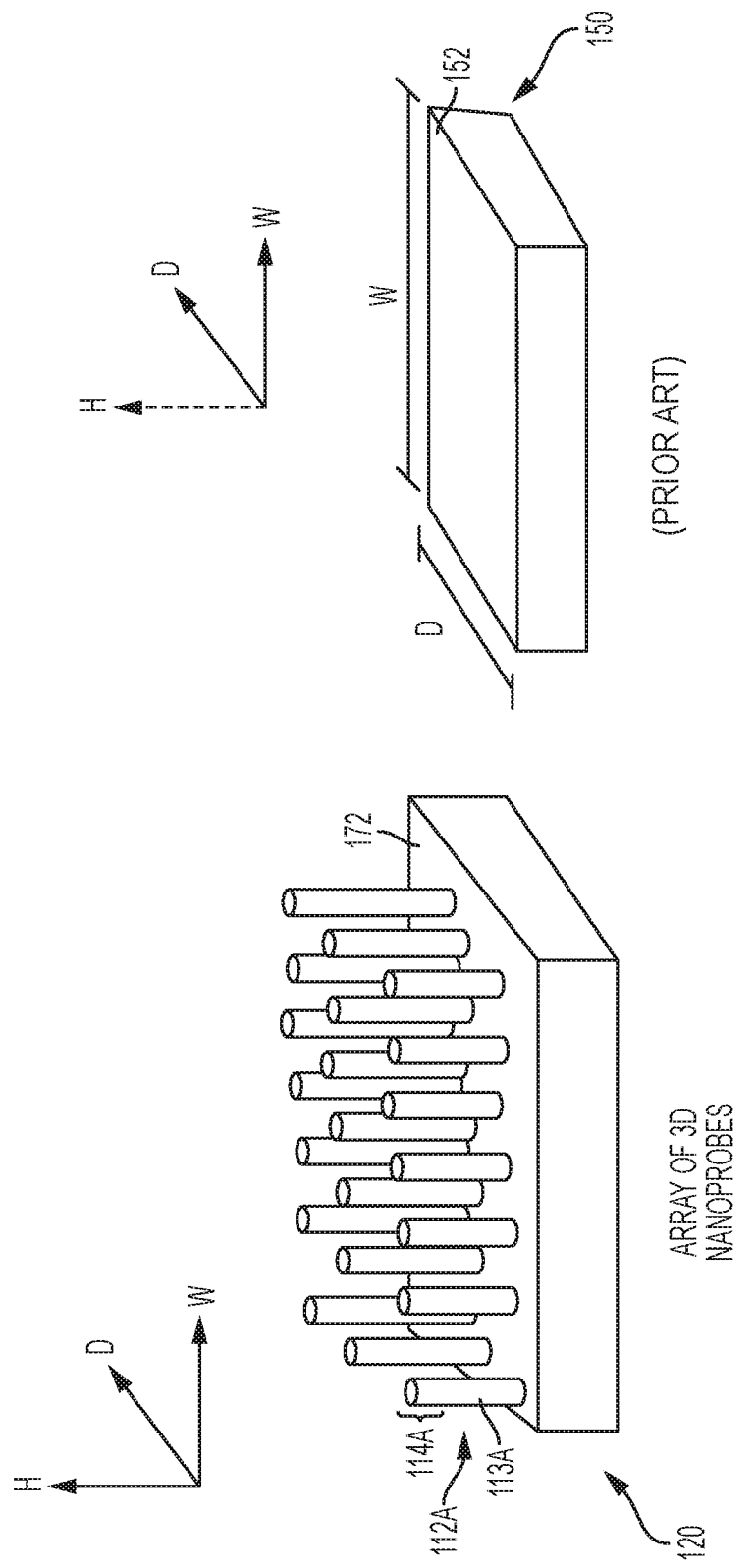
FIG. 1C depicts a block diagram of a known 2D substantially planar biosensor electrode and an array of 3D nanoprobe biosensor electrodes according to one or more embodiments of the invention.

FIG. 1C depicts a block diagram of a known biosensor electrode 150 having a 2D substantially planar sensing surface 152. FIG. 1C also depicts a block diagram of a biosensor electrode 170 having an array of 3D nanoprobes 112A formed on a 2D substantially planar surface 172 according to embodiments of the invention. For ease of illustration and explanation, the biosensor electrode 170 is depicted with an array of the cylindrical 3D nanoprobes 112A. However, the biosensor electrode 170 can be implemented with an array of the non-elongated pyramidal 3D nanoprobes 112B, the elongated pyramidal 3D nanoprobes 112C, the conical 3D nanoprobes 112D, or any combination and arrangement thereof.

As best depicted in FIGS. 1B and 1C, the 3D nanoprobe shapes 112A, 112B, 112C, 112D each define exterior surfaces 113A, 113B, 113C, 113D that each has a height (H) dimension, a width (W) dimension and a depth (D) dimension. The exterior surfaces 113A, 113B, 113C, 113D can be coated with a recognition element to function as sensing surfaces, and the sensing surface areas provided by the sensing surfaces 113A, 113B, 113C, 113D are determined by the H, W and D dimension of the sensing surfaces 113A, 113B, 113C, 113D. In some embodiments, the final configuration of the biosensor electrode 170 can leave the 2D substantially planar surface 172 exposed such that the surface 172 can also be coated with a recognition element to provide an additional sensing surface area for the biosensor electrode 170. The recognition element can be a biofilm material such as a receptor, enzyme, antibody, DNA or other type of capturing molecule that is biologically specific for the target analyte. The recognition element can be configured to detect, for example, ion concentration (e.g., pH) or the concentration of target biomolecules (e.g., DNA, microRNA, enzymes, antibodies, and the like). The phrase "target analyte" and variations thereof will be used herein to refer to an ion, a target molecule, or any other biological substance.

Accordingly, embodiments of the invention increase the number of electrode parameters that can be tuned in order to increase the sensing surface area, thus improving signal strength of the sensing surface, as well as the signal to noise ratio of the sensing surface. More specifically, the electrode parameters include, but are not limited to, providing 3D nanoprobes, the 3D shape of the 3D nanoprobe, the height dimension of the 3D nanoprobe, organizing multiple 3D nanoprobes in an array, organizing multiple 3D nanoprobes on a 2D electrode surface, organizing multiple 3D nanoprobes on a 2D electrode surface such that portions of the 2D electrode surface are exposed to provide sensing surface area in addition to the sensing surface areas provided by the 3D nanoprobes, and variations and combinations of the above. In the known biosensor electrode 150, the electrode parameters that can be tuned in order to increase the sensing surface area are limited to the width (W) dimension and the depth (D) dimension of the 2D substantially planar sensing surface 152, each of which would have the disadvantage of increasing the electrode's footprint.

The W, D and H dimensions of the 3D nanoprobes 112, 122, 112A, 112B, 112C, 112D can vary according to design considerations. For example, the W, D and H dimensions of the 3D nanoprobes 112, 122, 112A, 112B, 112C, 112D can be designed to have predetermined values, to have values within predetermined ranges, to have values having fixed ratios with respect to each other, or to have values based on any other consideration or combination of considerations in accordance with the functionality of the 3D nanoprobes 112, 122, 112A, 112B, 112C, 112D described herein.

Figure 2:
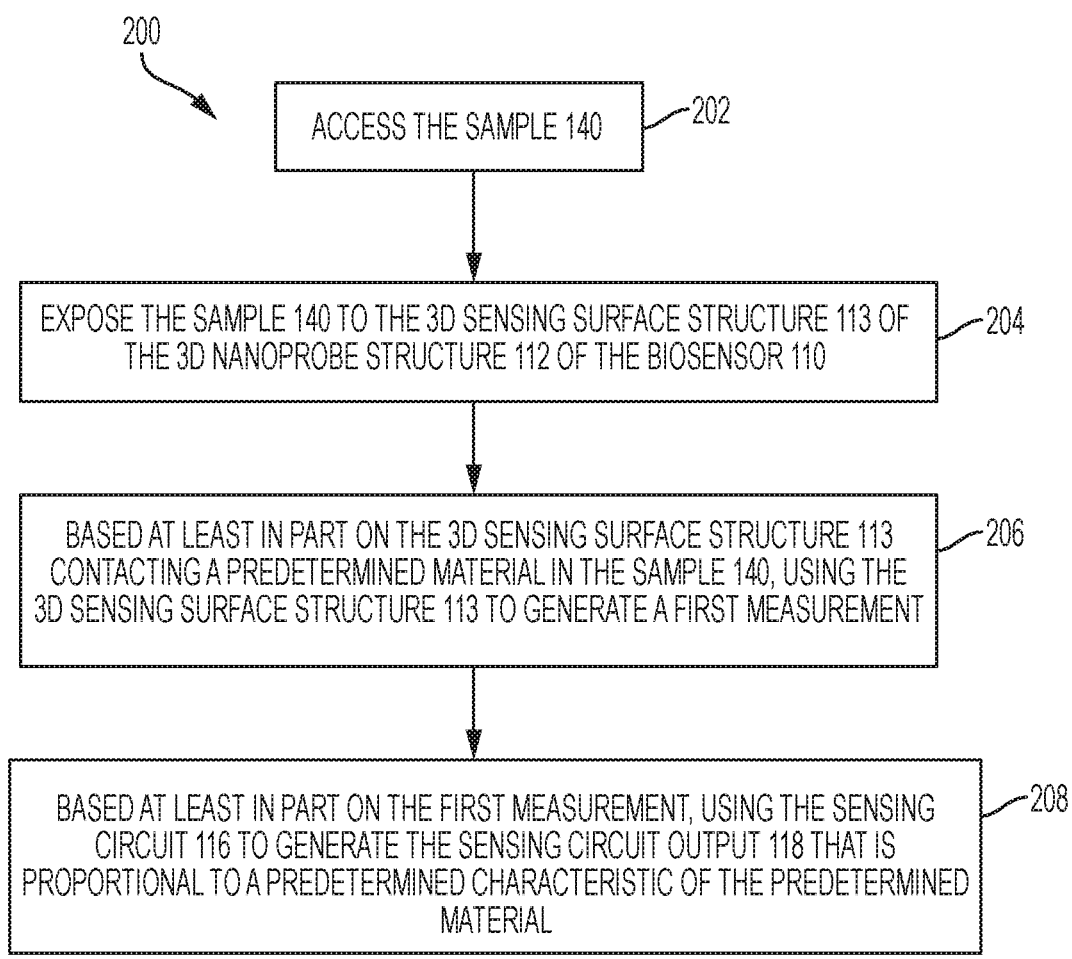
FIG. 2 depicts a flow diagram illustrating a method of using a biosensor having a 3D nanoprobe biosensor electrode according to one or more embodiments of the invention.

FIG. 2 is a flow diagram illustrating a method 200 of using the biosensor system 100 according to one or more embodiments of the invention. Block 202 accesses the sample 140. Block 204 exposes the sample 140 to the 3D sensing surface structure 113 of the 3D nanoprobe structure 112 of the biosensor 110. The biosensor 110 includes the sensing circuit 116 communicatively coupled to the 3D nanoprobe structure 112 and the 3D sensing surface structure 113. In block 206, based at least in part on the 3D sensing surface structure 113 contacting a predetermined material in the sample 140, the 3D sensing surface structure 113 generates a first measurement. In block 208, based at least in part on the first measurement, the sensing circuit 116 generates the sensing circuit output 118 that is proportional to a predetermined characteristic of the predetermined material.

In some embodiments of the invention, exposing the sample 140 to the 3D sensing surface structure 113 can be accomplished by placing the sensing surface structure 113 in the container 102, which contains the sample 140. In some embodiments of the invention, exposing the sample 140 to the 3D sensing surfaces structure 113 can be accomplished by applying sufficient pressure to cause the 3D nanoprobe structure 112 penetrate the cell wall 144 of the biological cell 142A and contact fluid 146 within the biological cell 142A. The pressure can be applied through the 3D nanoprobe structure 112, the biological cell 142, or both. In some embodiments of the invention, the biosensor 110 is moved closer to the biological cell 142A until the biosensor system 100 registers the measurement of the analyte of interest, which in some situations is only found within the biological cell 142A. Thus, it can be inferred that when the biosensor system 100 measures a nonzero amount of the material of interest, the biosensor 110 has penetrated the cell wall 144 and additional pressure to move the biosensor 110 farther is terminated. In some embodiments of the invention, in the case where the biological cell 142A is situated in a container 102 with a well-defined rigid bottom surface, the biosensor 110 is moved toward the biological cell 142A and the container unit 102 until the sensor probes 112 penetrate the cell wall 144 and motion is slowed by the bottom of the container 102. In some embodiments of the invention, the biosensor 110 includes an integral microscope that is used to determine the location of the biosensor probes 112 relative to the cell wall 144. The biosensor 112 with integral microscope is focused on the biological sample 140. In some embodiments of the invention, the sample 140 and the container 102 are configured on a movable table, similar to a conventional microscope, and the table is moved toward the bio sensor probes 112 until the biosensor probes 112 penetrate the cell wall 144.

In some embodiments of the invention, the above-described 3D nanoprobe structure is implemented as an array (e.g., array 170 shown in FIG. 1C) having multiple 3D nanoprobes 112A and multiple 3D sensing surfaces 113A.

Figure 3:
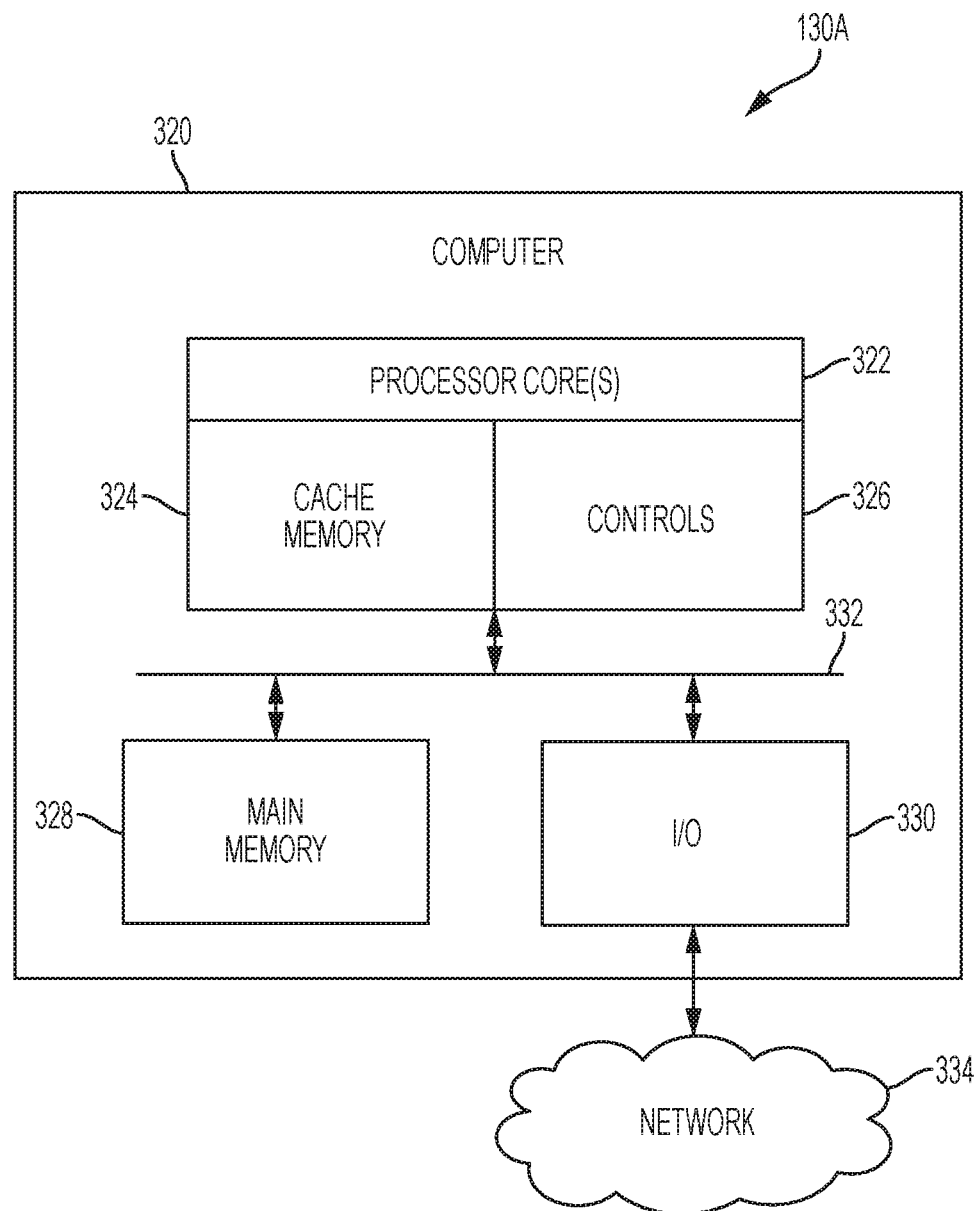
FIG. 3 depicts a block diagram showing additional details of the processor shown in FIG. 1A.

FIG. 3 depicts a more detailed example of how the processor 130 (shown in FIG. 1A) can be implemented as a computer system 130A including an exemplary computing device ("computer") 320 configured to receive the sensing circuit output 118 (shown in FIG. 1A) from the sensing circuit 116 (shown in FIG. 1A) and process/analyze the same in accordance with aspects of the present invention. In addition to computer 320, exemplary computer system 130A includes network 334, which connects computer 320 to additional systems (not depicted) and can include one or more wide area networks (WANs) and/or local area networks (LANs) such as the Internet, intranet(s), and/or wireless communication network(s). Computer 320 and additional systems are in communication via network 334, e.g., to communicate data between them.

Exemplary computer 320 includes processor cores 322, main memory ("memory") 328, and input/output component(s) 330, which are in communication via bus 332. Processor cores 322 includes cache memory ("cache") 324 and controls 326. Cache 324 can include multiple cache levels (not depicted) that are on or off-chip from processor 322. Memory 324 can include various data stored therein, e.g., instructions, software, routines, etc., which, e.g., can be transferred to/from cache 324 by controls 326 for execution by processor 322. Input/output component(s) 330 can include one or more components that facilitate local and/or remote input/output operations to/from computer 320, such as a display, keyboard, modem, network adapter, etc. (not depicted).

FIGS. 4-13 illustrate an exemplary method for forming a biosensor 110A having 3D nanoprobes according to embodiments of the invention. The biosensor 110A shown in FIGS. 4-13 is an example implementation of the first and second biosensors 110, 120 shown in FIG. 1A. In the example illustrated in FIGS. 4-13, the biosensor 110A is implemented as a semiconductor device, and more specifically as a field effect transistor (FET) having a 3D structured nanoprobe that can in some embodiments be configured to penetrate a cellular wall and make direct intracellular measurements from inside the cell. General descriptions of semiconductor device fabrication processes that can be utilized in implementing the biosensor 110A according to embodiments of the present invention will now be provided. Although specific fabrication operations used in implementing the biosensor 110A can be individually known, the described combination of operations and/or resulting structures of the present invention are unique. Thus, the unique combinations of the operations described according to the present invention utilize a variety of individually known physical and chemical processes performed on a semiconductor (e.g., silicon) substrate, some of which are described in more detail in the immediately following paragraphs.

Figure 4:
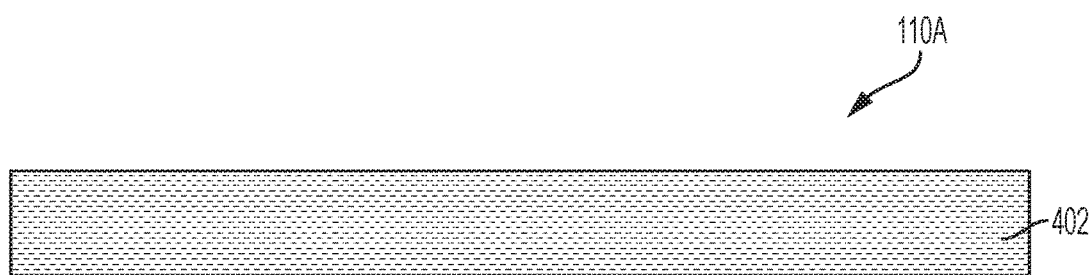
FIG. 4 depicts a cross-sectional view of a 3D nanoprobe biosensor after an initial fabrication stage according to one or more embodiment of the invention.

FIG. 4 depicts a cross-sectional view of the biosensor 110A after an initial fabrication stage according to embodiments of the invention. In the fabrication stage shown in FIG. 4, a substrate 402 is formed from semiconductor material using conventional fabrication techniques. In some embodiments some embodiments of the invention, the substrate 402 is formed from bulk silicon material. In some embodiments of the invention, the substrate 402 is implemented in a semiconductor-on-insulator (SOI) substrate arrangement. Non-limiting examples of suitable materials for the semiconductor material of the substrate 402 include Si (silicon), strained Si, SiC (silicon carbide), Ge (germanium), SiGe (silicon germanium), SiGeC (silicon-germanium-carbon), Si alloys, Ge alloys, III-V materials (e.g., GaAs (gallium arsenide), InAs (indium arsenide), InP (indium phosphide), or aluminum arsenide (AlAs)), II-VI materials (e.g., CdSe (cadmium selenide), CdS (cadmium sulfide), CdTe (cadmium telluride), ZnO (zinc oxide), ZnSe (zinc selenide), ZnS (zinc sulfide), or ZnTe (zinc telluride)), or any combination thereof. Other non-limiting examples of semiconductor materials include III-V materials, for example, indium phosphide (InP), gallium arsenide (GaAs), aluminum arsenide (AlAs), or any combination thereof. The III-V materials can include at least one "III element," such as aluminum (Al), boron (B), gallium (Ga), indium (In), and at least one "V element," such as nitrogen (N), phosphorous (P), arsenic (As), antimony (Sb).

Figure 5:
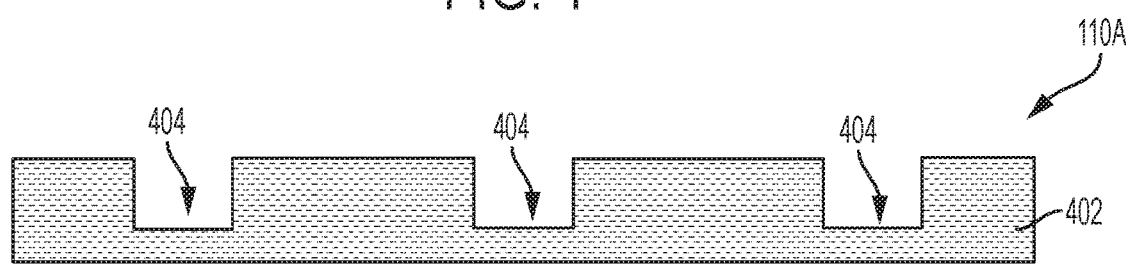
FIG. 5 depicts a cross-sectional view of the 3D nanoprobe biosensor after a fabrication stage according to one or more embodiment of the invention.

FIG. 5 depicts a cross-sectional view of the biosensor 110A after a fabrication stage in which shallow trench isolation (STI) regions 404 are formed in the substrate 402 from an oxide material using conventional techniques related to semiconductor device and IC fabrication. In one or more embodiments, the STI regions 404 can be formed by forming a thin oxidation layer followed by deposition of silicon nitride. Conventional lithography and dry etch (e.g., RIE) processes can be used to form shallow trenches extending through the silicon nitride and the oxide and into the substrate 402. Sidewalls of the shallow trenches are oxidized using a thermal oxidation process, and a HDP or CVD process is used to overfill the shallow trenches with oxide. A CMP process is applied to remove oxide from the horizontal surfaces of the silicon nitride. The silicon nitride is removed using, for example, hot phosphoric acid, and the pad oxide is removed using, for example, hydrofluoric acid, which results in the STI regions 404 formed from oxide material.

Figure 6:
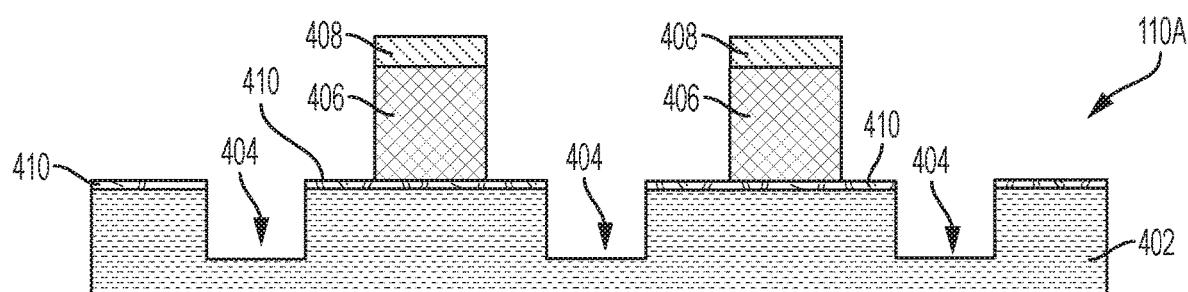
FIG. 6 depicts a cross-sectional view of the 3D nanoprobe biosensor after a fabrication stage according to one or more embodiment of the invention.

FIG. 6 depicts a cross-sectional view of the biosensor 110A after a fabrication stage in which a gate dielectric (e.g., SiO$_2$) 410, a poly silicon gate electrode 406, and a gate hard mask (e.g., SiN) 408 have been formed over the substrate 402 using conventional techniques related to semiconductor device and IC fabrication. Conventional lithography and dry etch (e.g., RIE) processes are used to form the poly silicon gate electrode 406. A poly silicon material is deposited, and the lithography process is used to transfer features of a photoresist layer into the poly silicon material by the dry etch process. The dry etch is stopped on the upper surface of the gate dielectric layer 410.

Figure 7:
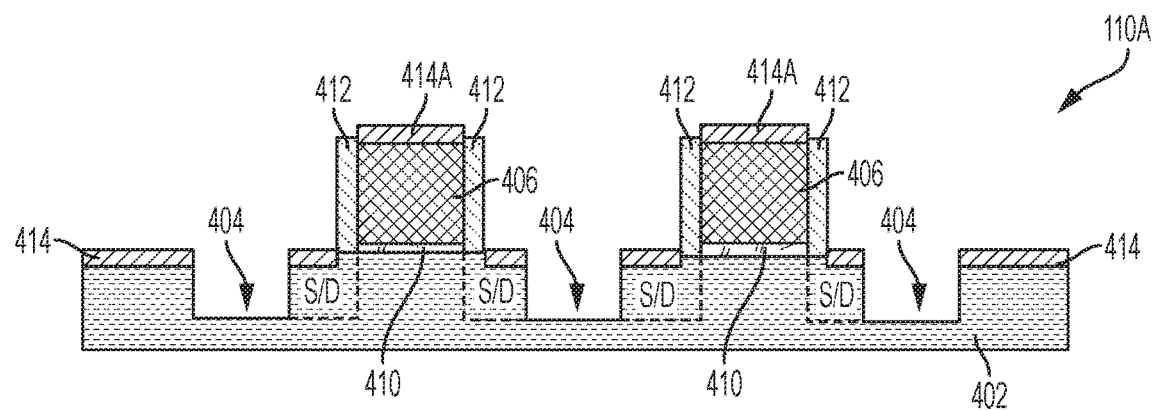
FIG. 7 depicts a cross-sectional view of the 3D nanoprobe biosensor after a fabrication stage according to one or more embodiment of the invention.

FIG. 7 depicts a cross-sectional view of the biosensor 110A after a fabrication stage in which portions of the gate dielectric 410 and the hard masks 408 have been removed, and silicide layers 414, 414A and spacers 412 have been formed using conventional techniques related to semiconductor device and IC fabrication. Conventional CMOS processing (e.g., ion implantation) is used to form source/drain (S/D) regions 702, which includes S/D extension regions. The S/D regions 702 are activated by a RTA process.

Figure 8:
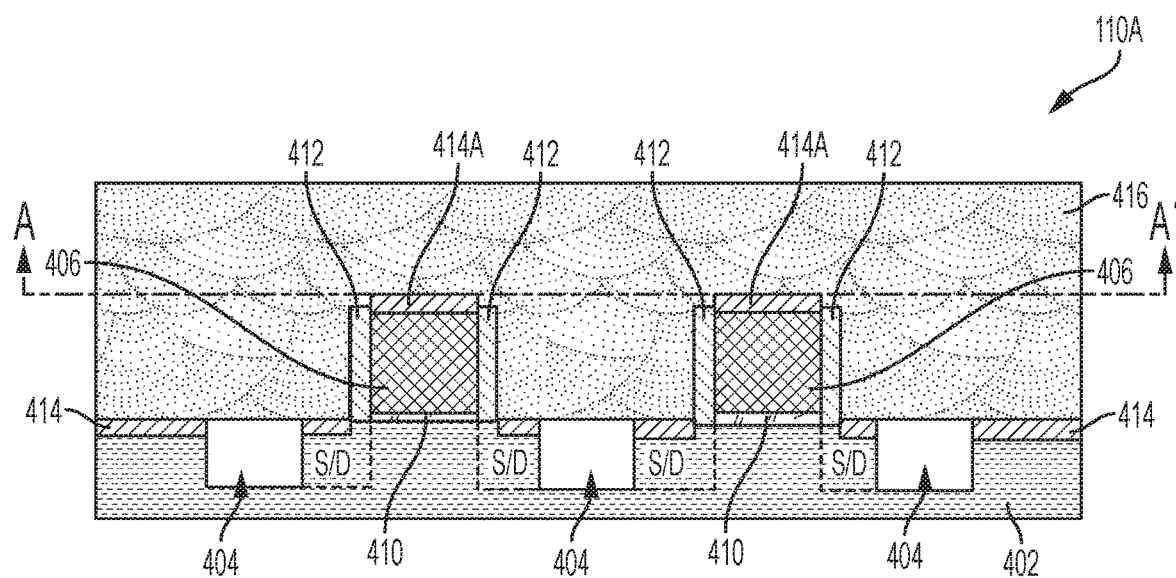
FIG. 8 depicts a cross-sectional view of the 3D nanoprobe biosensor after a fabrication stage according to one or more embodiment of the invention.

FIG. 8 depicts a cross-sectional view of the biosensor 110A after a fabrication stage in which an oxide fill 416 has been deposited over the biosensor 110A and polished back to form a flat oxide surface. In one or more embodiments, the oxide fill is deposited using a HDP or SACVD deposition process. A timed CMP can be applied to form the flat surface of the oxide fill 416.

Figure 9:
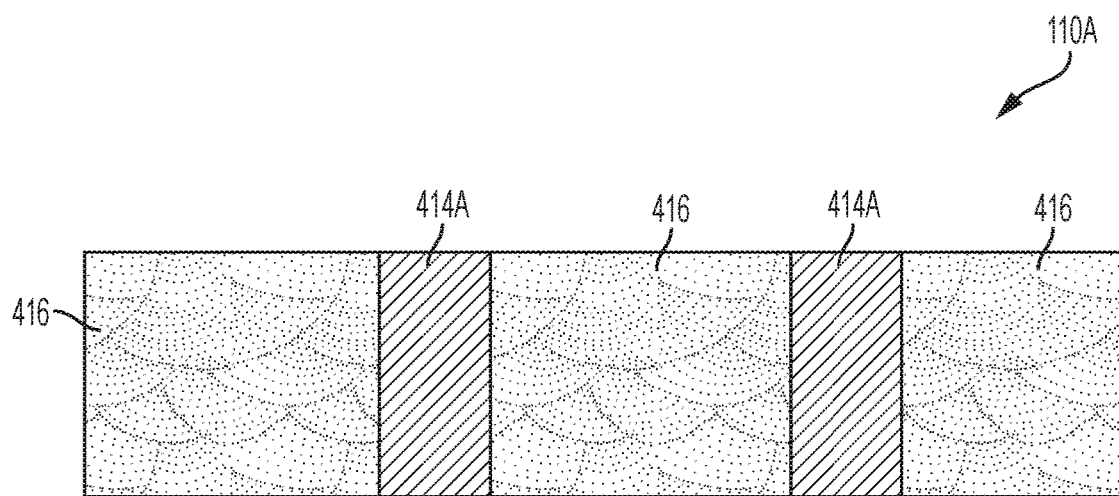
FIG. 9 depicts a top-down view taken along line A-A' of the 3D nanoprobe biosensor shown in FIG. 8.

FIG. 9 depicts a top-down view taken along line A-A' of the biosensor 110A shown in FIG. 8.

Figure 10:
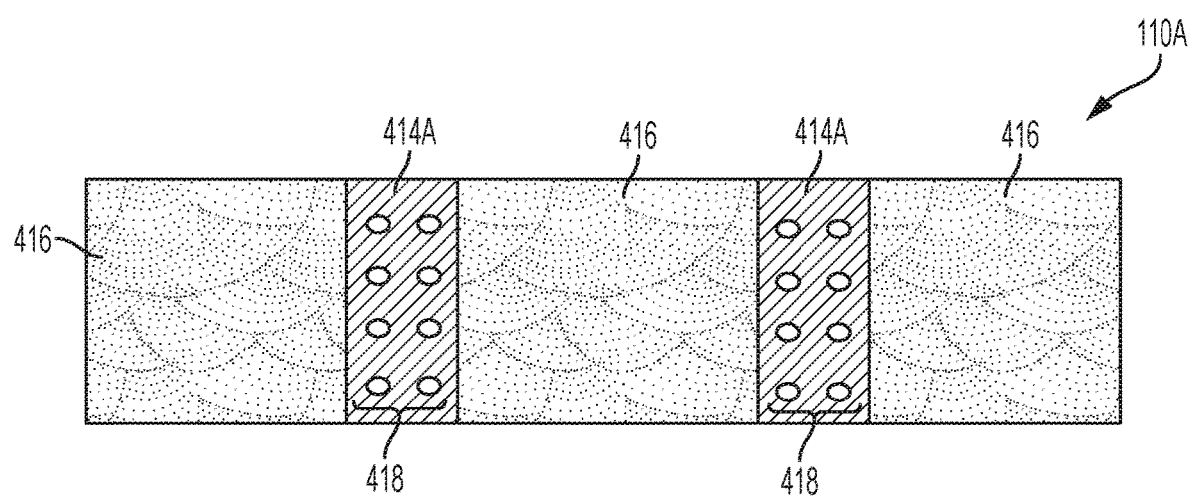
FIG. 10 depicts a top-down view taken along line A-A' of the 3D nanoprobe biosensor shown in FIG. 8 after a fabrication stage according to one or more embodiment of the invention.

FIG. 10 depicts a top-down view taken along line A-A' of the biosensor 110A shown in FIG. 8 after a fabrication stage in which conventional lithography and dry etch processes are used to form contact holes 418 extending through the oxide fill 416 (shown in FIG. 8) and over the gate regions 406.

Figure 11:
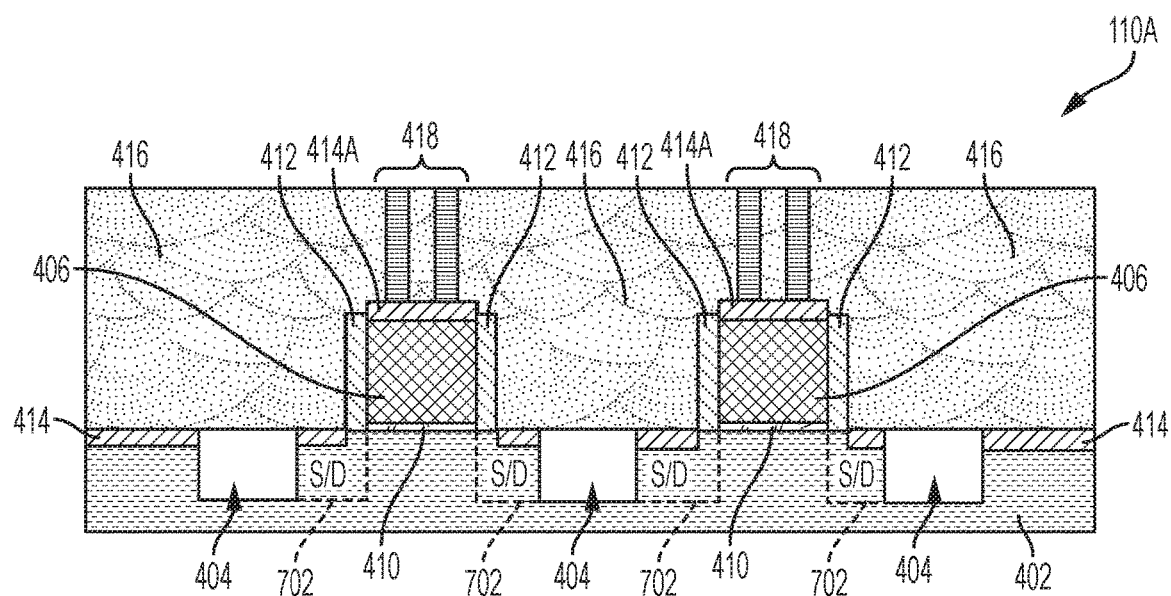
FIG. 11 depicts a cross-sectional view of the 3D nanoprobe biosensor after a fabrication stage according to one or more embodiment of the invention.

FIG. 11 depicts a cross-sectional view of the biosensor 110A shown in FIG. 10 further illustrating the contact holes 418 extending through the oxide fill 416 (shown in FIG. 8) and over the gate regions 406 and portions of the S/D regions 702.

Figure 12:
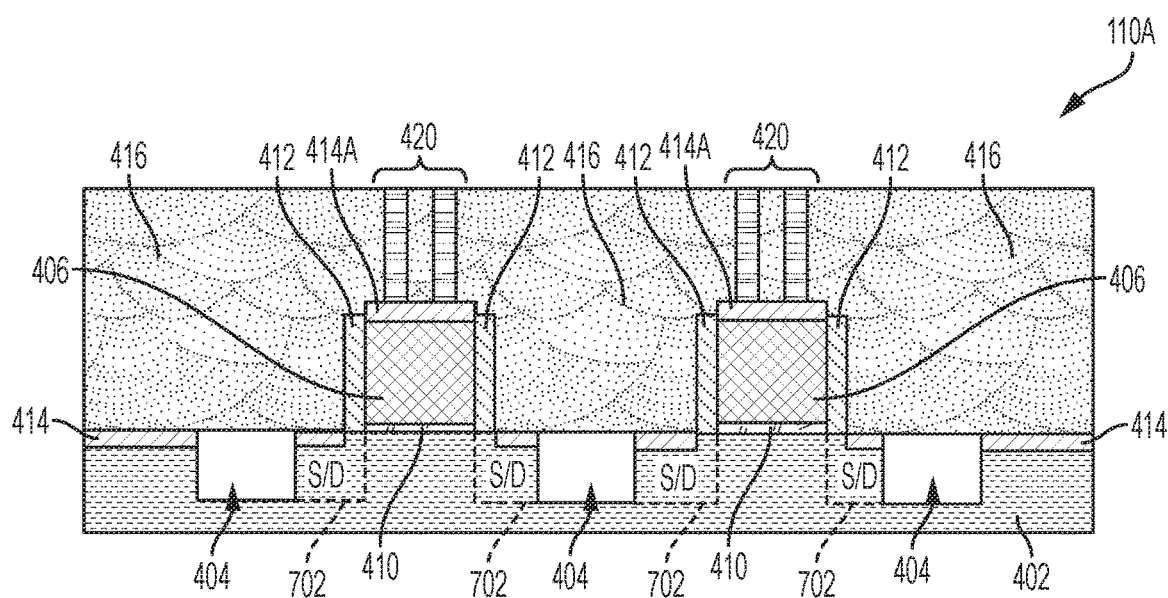
FIG. 12 depicts a cross-sectional view of the 3D nanoprobe biosensor after a fabrication stage according to one or more embodiment of the invention.

FIG. 12 depicts a cross-sectional view of the biosensor 110A after a fabrication stage in which the contact holes 418 are lined with a liner (e.g., TaN) that will function as the recognition element. The recognition element can be a biofilm material such as a receptor, enzyme, antibody, DNA or other type of capturing molecule that is biologically specific for the target analyte. The recognition element can be configured to detect, for example, ion concentration (e.g., pH) or the concentration of target biomolecules (e.g., DNA, microRNA, enzymes, antibodies, and the like). The phrase "target analyte" and variations thereof will be used herein to refer to an ion, a target molecule, or any other biological substance. The remaining volumes of the holes 418 are filled with a metal (e.g., W) by ALD or CVD processing to form cylindrical 3D nanoprobes 420 according to embodiments of the invention.

Figure 13:
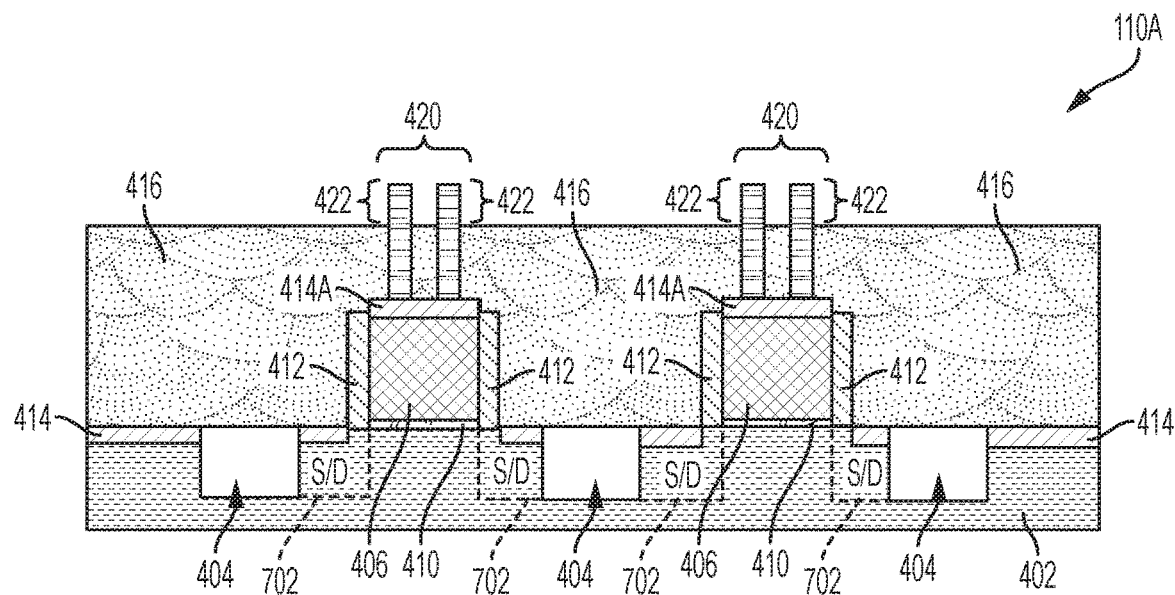
FIG. 13 depicts a cross-sectional view of the 3D nanoprobe biosensor after a fabrication stage according to one or more embodiment of the invention.

FIG. 13 depicts a cross-sectional view of the biosensor 110A after a fabrication stage in which the oxide fill 416 has been further recessed using a hafnium (Hf) dip or RIE process to expose end regions 422 of the cylindrical 3D nanoprobes 420. Recessing the oxide fill 416 can be controlled and tuned to expose a desired amount of the H dimension of the cylindrical 3D nanotubes 420. In some embodiments, the entire H dimension of the cylindrical 3D nanotubes 420 can be exposed to expose the entire sensing surface 113A (best shown in FIG. 1B) of the cylindrical 3D nanoprobes 420. In some embodiments, the top surface of the silicide layers 414A can be exposed and coated with a recognition element to provide another sensing surface to supplement the sensing surface 113A (best shown in FIG. 1B) of the cylindrical 3D nanoprobes 420.

FIGS. 14-18 illustrate an exemplary method for forming a biosensor 110B according to embodiments of the invention. The biosensor 110B shown in FIGS. 14-18 is an example implementation of the biosensor 110 shown in FIG. 1A. In the example illustrated in FIGS. 14-18, the biosensor 110B is implemented as a semiconductor device, and more specifically as a FET having an elongated pyramidal 3D nanoprobe of the type shown at 112C in FIG. 1B. General descriptions of semiconductor device fabrication processes that can be utilized in implementing the biosensor 110B according to embodiments of the present invention will now be provided. Although specific fabrication operations used in implementing the biosensor 110B can be individually known, the described combination of operations and/or resulting structures of the present invention are unique. Thus, the unique combinations of the operations described according to the present invention utilize a variety of individually known physical and chemical processes performed on a semiconductor (e.g., silicon) substrate, some of which are described in more detail in the immediately following paragraphs.

Figure 14:
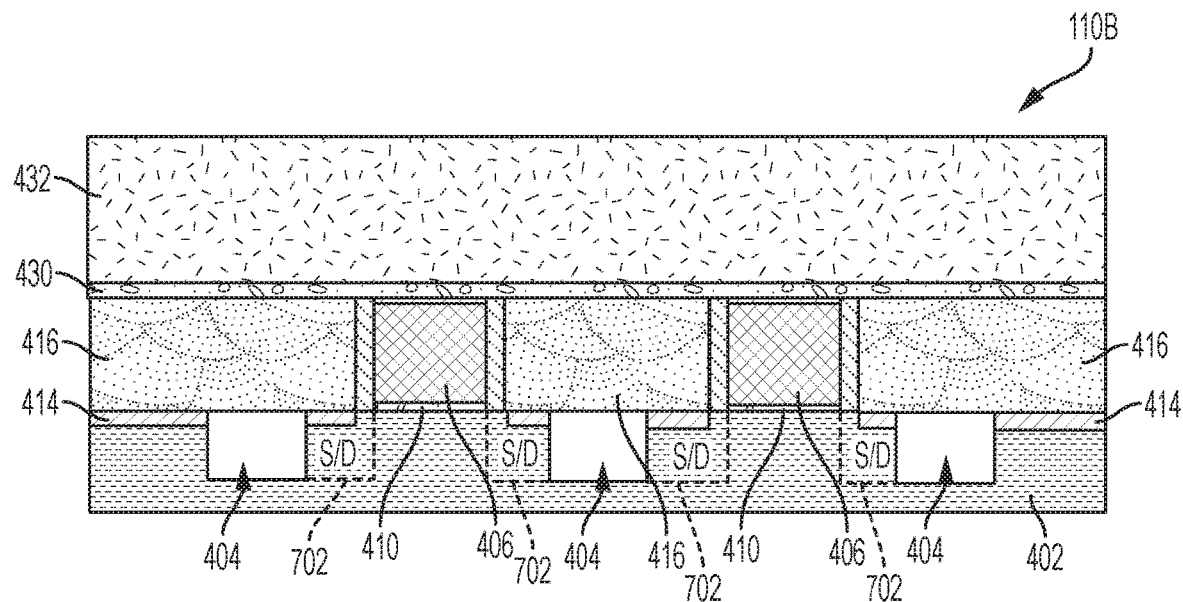
FIG. 14 depicts a cross-sectional view of the 3D nanoprobe biosensor after an alternative fabrication stage according to one or more embodiment of the invention.

FIG. 14 depicts a cross-sectional view of the biosensor 110B after a fabrication stage according to one or more embodiment of the invention. In the biosensor 110B depicted in FIG. 14, the same fabrication operations depicted in FIGS. 4-8 have been performed except the oxide fill 416 has been polished back to the silicide layers 414A, and a liner (e.g., TiTiN or TaTaN) 430 and a metal layer (e.g., Al or W) 432 have been deposited over the biosensor 110B.

Figure 15:
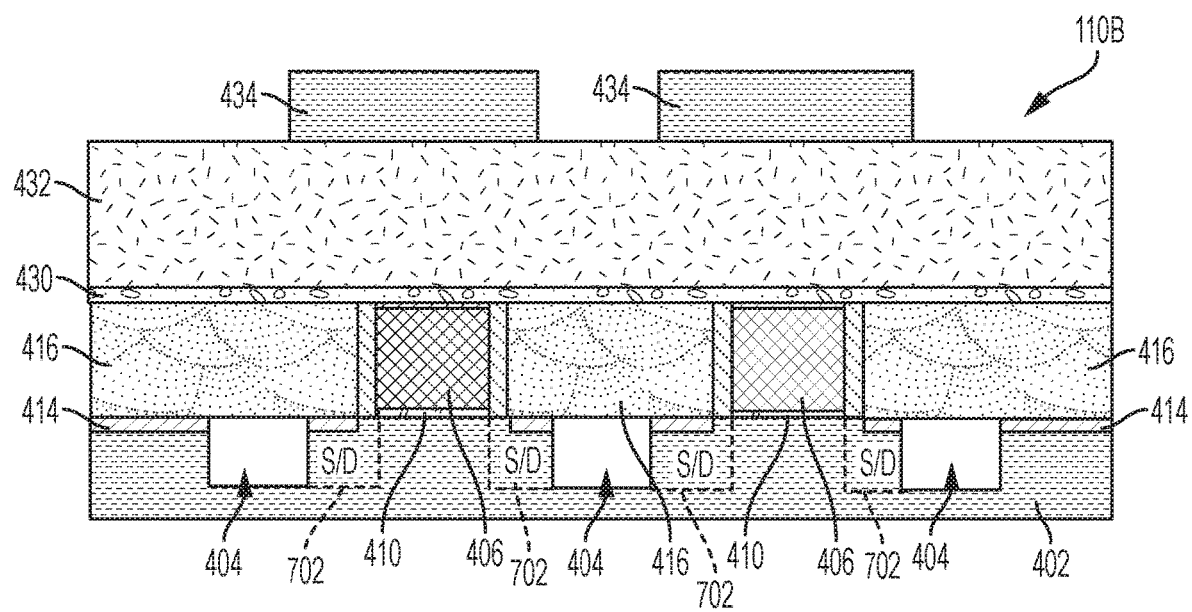
FIG. 15 depicts a cross-sectional view of the 3D nanoprobe biosensor after an alternative fabrication stage according to one or more embodiment of the invention.

FIG. 15 depicts a cross-sectional view of the biosensor 110B after a fabrication stage in which a resist pattern 434 is formed over the metal layer 432.

Figure 16:
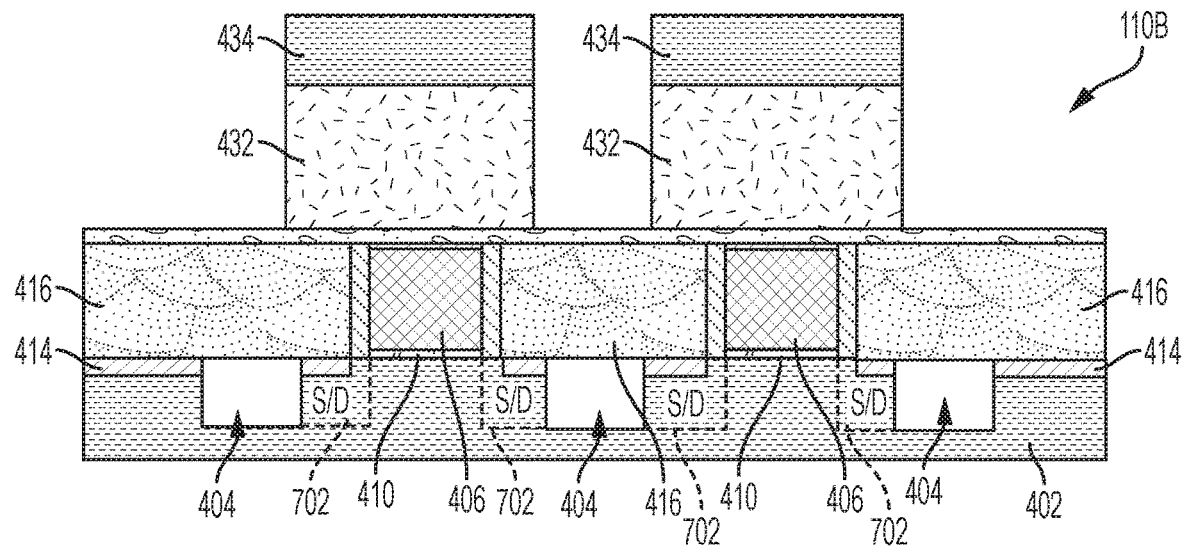
FIG. 16 depicts a cross-sectional view of the 3D nanoprobe biosensor after an alternative fabrication stage according to one or more embodiment of the invention.

FIG. 16 depicts a cross-sectional view of the biosensor 110B after a fabrication stage in which the metal layer 432 has been etched to transfer the resist pattern 434 to the metal layer 432.

Figure 17:
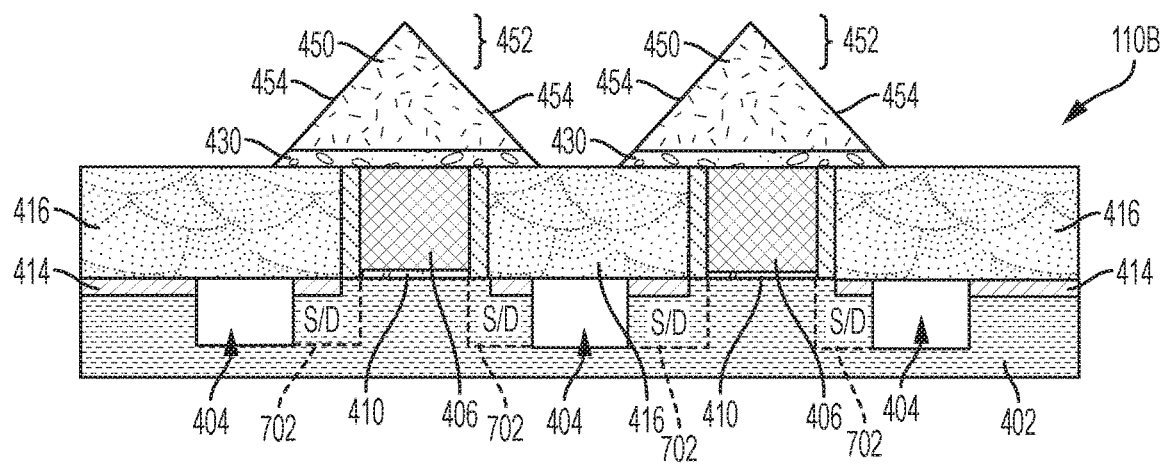
FIG. 17 depicts a cross-sectional view of the 3D nanoprobe biosensor after an alternative fabrication stage according to one or more embodiment of the invention.
Figure 18:
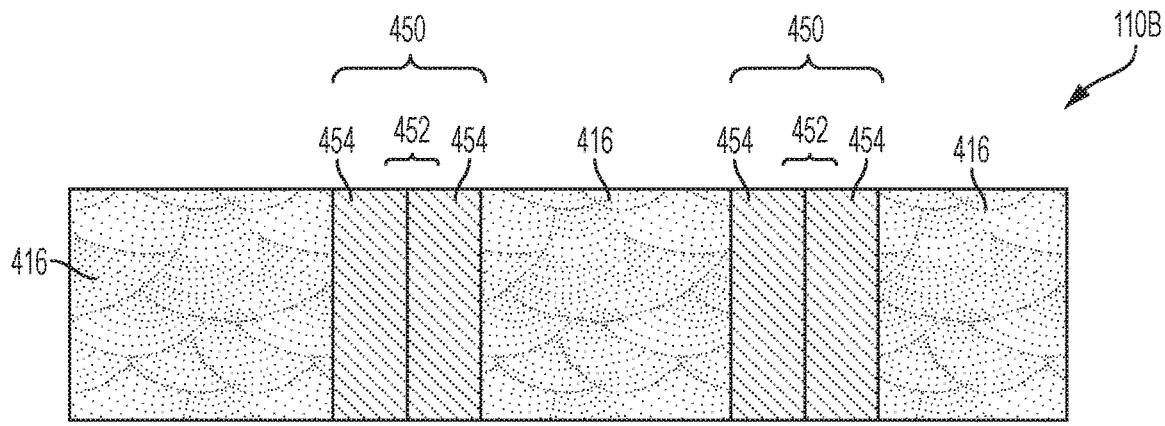
FIG. 18 depicts a top-down view of the 3D nanoprobe biosensor shown in FIG. 17.

FIG. 17 depicts a cross-sectional view of the biosensor 110B after a fabrication stage in which the metal layers 432 are etched into a desired shape, which can include, for example, the shapes of any of the 3D nanoprobes 112A, 112B, 112C, 112D shown in FIG. 1C. FIG. 18 depicts a top-down view of the biosensor 110B shown in FIG. 17. In the embodiment depicted in FIGS. 17 and 18, the metal layers 432 have been etched into the shape of elongated pyramidal 3D nanoprobes 450 having sensing surface areas 454 and apex regions 452. In some embodiments, the metal layers 432 are shaped through ion beam etching (IBE) performed at the appropriate angle such as about 45 degrees. The sensing surface areas 454 and/or the apex regions 452 can be coated with a variety of material to make them function as a recognition element. The particular coating material is selected to match the specific application.

Figure 19:
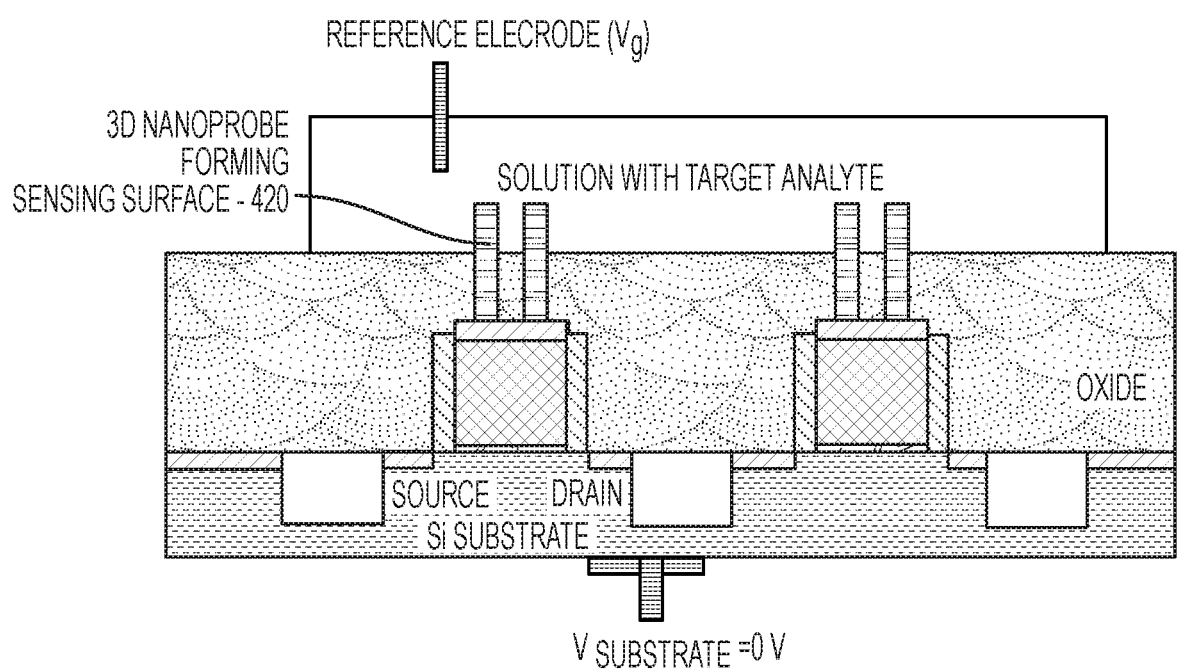
FIG. 19 depicts a schematic diagram illustrating a method of using a biosensor system having a 3D nanoprobe according to one or more embodiments of the invention.

FIG. 19 depicts a schematic diagram illustrating a configuration for using the biosensor 110A having 3D nanoprobes 420 according to one or more embodiments of the invention. The current from the source to the drain is the sensing signal. The gate voltage is applied at a reference electrode, and the source and substrate voltages are set at zero (0) V. The drain voltage is set at a small (~25 mV) voltage. The drain voltage is positive for n-type FETs and negative voltage for p-type FETs. The 3D sensing surface of the 3D nanoprobes can be coated with TiN for pH sensing, AgCl for Cl detection, or gold for detecting biomolecules using thiol chemistry.

Figure 20:
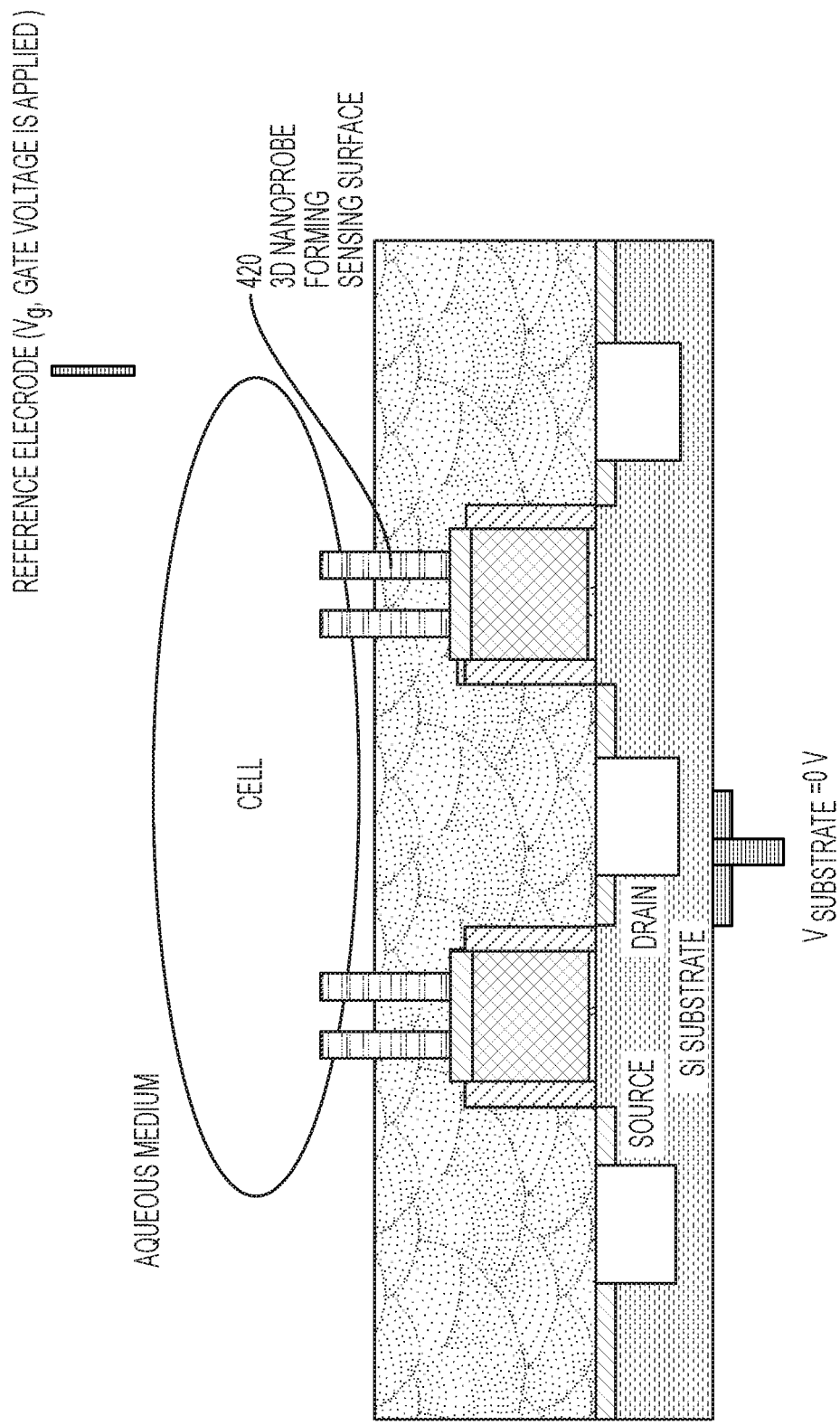
FIG. 20 depicts a schematic diagram illustrating a method of using a biosensor system having a 3D nanoprobe according to one or more embodiments of the invention.

FIG. 20 depicts a schematic diagram illustrating a configuration for using the biosensor 110A having 3D nanoprobes 420 according to one or more embodiments of the invention. The current from the source to the drain is the sensing signal. The gate voltage is applied at a reference electrode, and the source and substrate voltages are set at zero (0) V. The drain voltage is set at a small (~25 mV) voltage. The drain voltage is positive for n-type FETs and negative voltage for p-type FETs. The 3D sensing surface of the 3D nanoprobes can be coated with TiN for pH sensing, AgCl for Cl detection, or gold for detecting biomolecules using thiol chemistry. In the embodiment depicted in FIG. 20, the 3D nanoprobe is provide with a width dimension (e.g., about 100 nm) that facilitates the 3D nanoprobe penetrating a cellular wall to contact and provide measurements from the fluid within the cell. A typical cell size is about 5×5 um$^2$. In some embodiments, sufficient pressure is applied to cause the 3D nanoprobe structure 112A to penetrate the cell wall of the biological cell and contact fluid within the biological cell. The pressure can be applied through the 3D nanoprobe structure, the biological cell, or both, using the various procedures previously described in connection with the biosensor system 100 shown in FIG. 1A.

Although the present invention is primarily disclosed in connection with use in human subjects, the teachings of the present invention can be used in organisms that include but are not limited to animals, reptiles and invertebrates. Additionally, the solution with the target analyte can be any aqueous environment or body of water, including oceans, lakes, streams and ponds.

Thus it can be seen from the foregoing detailed description that the present invention provides a number of technical benefits and effects. Embodiments of the invention provide a FET-based biosensor where the gate of the FET is shaped in a 3D nanoprobe structure such as a cylinder, a pyramid, a cone, or the like. The 3D nanoprobe can be coated with a recognition element (e.g., TiN) for measuring pH. The 3D nanoprobe can be coated with another recognition element (e.g., Au) or measuring biomolecules using thiol chemistry. For example, for detecting DNA, the gold surface can be functionalized with single strand DNA complimentary to the target DNA. In some embodiments, the 3D nanoprobe is provide with a width dimension (e.g., about 100 nm) and other structure features that facilitates the 3D nanoprobe penetrating a cellular wall to contacts and provide measurements from the fluid within the cell. A typical cell size is about 5×5 um$^2$. Accordingly, embodiments of the invention provide more sensing surface area, which improves the efficiency with which analytes of interest bind to the sensing surface, improves the signal strength, and improves the signal to noise ratio. Embodiments of the invention are also directed to methods for fabricating the FET and 3D nanoprobe structure, as well as methods for using the FET and 3D nanoprobe structure.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the present invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A sensor comprising:
a sensing circuit comprising a field effect transistor (FET) having a gate structure; and
a first probe on a top surface of the gate structure and communicatively coupled to the sensing circuit and the gate structure;
where a portion of the top surface of the gate structure comprises a two-dimensional (2D) sensing surface;
where the first probe comprises a first three-dimensional (3D) sensing surface; and
a first liner having a first portion formed on the 2D sensing surface and a second portion formed on the first 3D sensing surface, wherein the first portion is separate from the second portion, wherein the first liner comprises a first recognition element having a first recognition element sensing characteristic comprising, upon the first portion on the 2D sensing surface and the second portion on the first 3D sensing surface interacting with a predetermined material, generating a first measurement.

2. The sensor of claim 1, where the first 3D sensing surface can penetrate through a wall of a biological cell and contact fluid within the biological cell.

3. The sensor of claim 1, where the sensing circuit, based at least in part on the first measurement, generates a sensing circuit output.

4. The sensor of claim 3, where the sensing circuit output is proportional to a predetermined characteristic of the predetermined material.

5. The sensor of claim 3, where:
the first measurement comprises a voltage;
the FET is configured to receive the voltage at the gate structure of the FET; and
the sensing circuit output comprises a current flow from a source of the FET to a drain of the FET.

6. The sensor of claim 1, where a shape of the first 3D sensing surface comprises:
a pyramid;
a cone; or
a cylinder.

7. The sensor of claim 6, where:
the pyramid or the cone includes an apex; and
the apex can penetrate through a wall of a biological cell and contact fluid within the biological cell.

8. The sensor of claim 6, where:
the cylinder comprises an exposed end; and
the exposed end can penetrate through a wall of a biological cell and contact fluid within the biological cell.

9. The sensor of claim 1, wherein:
the gate structure comprises a silicide layer; and
the top surface of the gate structure comprises a top surface of the silicide layer.

10. The sensor of claim 1 further comprising:
a second probe on the top surface of the gate structure and communicatively coupled to the sensing circuit and the gate structure;
where a second portion of the top surface of the gate structure comprises a second 2D sensing surface;
where the second probe comprises a second 3D sensing surface;
a second liner having a third portion formed on the second 2D sensing surface and a third portion formed on the second 3D sensing surface, wherein the second portion is separate from the third portion, wherein the second liner comprises a second recognition element having a second recognition element sensing characteristic comprising, upon the third portion on the second 2D sensing surface and the fourth portion on the second 3D sensing surface interacting with the predetermined material, generating a second measurement.

* * * * *